US012569450B2

(12) United States Patent
Palomba et al.

(10) Patent No.: US 12,569,450 B2
(45) Date of Patent: Mar. 10, 2026

(54) NANOPARTICLES FOR MEDICAL AND DIAGNOSTIC APPLICATIONS

(71) Applicant: Fondazione Istituto Italiano di Tecnologia, Genoa (IT)

(72) Inventors: Roberto Palomba, Genoa (IT); Paolo Decuzzi, Bari (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 732 days.

(21) Appl. No.: 17/776,481

(22) PCT Filed: Nov. 9, 2020

(86) PCT No.: PCT/IB2020/060519
§ 371 (c)(1),
(2) Date: May 12, 2022

(87) PCT Pub. No.: WO2021/094893
PCT Pub. Date: May 20, 2021

(65) Prior Publication Data
US 2023/0000784 A1      Jan. 5, 2023

(30) Foreign Application Priority Data

Nov. 13, 2019     (IT) ........................ 102019000021090

(51) Int. Cl.
*A61K 9/51*          (2006.01)
*A61K 45/06*        (2006.01)
*B82Y 5/00*          (2011.01)
*B82Y 40/00*        (2011.01)

(52) U.S. Cl.
CPC .......... *A61K 9/5169* (2013.01); *A61K 9/5123* (2013.01); *A61K 9/5192* (2013.01); *A61K 45/06* (2013.01); *B82Y 5/00* (2013.01); *B82Y 40/00* (2013.01)

(58) Field of Classification Search
None
See application file for complete search history.

(56) References Cited

FOREIGN PATENT DOCUMENTS

WO      WO-2018234489 A1 * 12/2018    ........... A61K 33/385

OTHER PUBLICATIONS

Vincenzi, B., Armento, G., Spalato Ceruso, M., Catania, G., Leakos, M., Santini, D., . . . Tonini, G. (2016). Drug-induced hepatotoxicity in cancer patients—implication for treatment. Expert Opinion on Drug Safety, 15(9), 1219-1238. https://doi.org/10.1080/14740338. 2016.1194824 (Year: 2016).*
Ahern, Holly. Biochemical, Reagent Kits Offer Scientists Good Return on Investment. The scientist, vol. 9, p. 20, Jul. 24, 1995. (retrieved from https://www.the-scientist.com/technology/biochemical-reagents-kits-offer-scientists-good-return-on-investment-58425) (Year: 1995).*
Cai, P. et al., "Methyl palmitate: Inhibitor of phagocytosis in primary rat Kupffer cells" Science Direct, Toxicology, Jun. 1, 2005. Vol. 210, No. 2-3, pp. 197-204. (8 pages).
An, F. "Strategies for Preparing Albumin-based Nanoparticles for Multifunctional Bioimaging and Drug Delivery" Theranostics. Jan. 1, 2017., vol. 7, No. 15, pp. 3667-3689 (23 pages).
Mantawy, E. et al., "Insights antifibrotic mechanism of methyl palmitate: Impact on nuclear factor kappa B and proinflammatory cytokines", Toxicology and Applied Pharmacology, Academic Pres, October 25, 2011., vol. 258, No. 1, pp. 134-144 (11 pages).
International Search Regan for PCT/IB2020/060519, dated Jan. 20, 2021 (3 pages).
Written Opinion of the ISA for PCT/IB2020/060519, dated Jan. 20, 2021 (6 pages).

* cited by examiner

*Primary Examiner* — Ali Soroush
*Assistant Examiner* — Afua Bamfoaa Boateng
(74) *Attorney, Agent, or Firm* — Nixon & Vanderhye, PC

(57) ABSTRACT

The present disclosure provides nanoparticles comprising methyl palmitate and at least one serumglobular protein and uses thereof.

6 Claims, 9 Drawing Sheets

NANOPARTICLES FOR MEDICAL AND DIAGNOSTIC APPLICATIONS

This application is the U.S. national phase of International Application No. PCT/IB2020/060519 filed Nov. 9, 2020, which designated the U.S. and claims priority to IT 102019000021090 filed Nov. 13, 2019, the entire contents of each of which are hereby incorporated by reference.

FIELD OF THE INVENTION

The present description concerns biocompatible nanoparticles for medical and diagnostic applications.

TECHNOLOGICAL BACKGROUND

Nanomedicine is a branch of medicine that applies the knowledge and tools of nanotechnology to the prevention and treatment of disease. Nanomedicine involves the use of nanoscale materials, such as for example biocompatible nanoparticles.

One of the main challenges in successfully using nanoparticles for drug delivery and biomedical imaging is overcoming biological barriers.

The Mononuclear Phagocytic System (MPS) is certainly a major biological barrier to be overcame in successfully delivering sufficient payloads to the original biological target. Any nanoparticles, regardless of its material composition and physio-chemical properties, is subject to recognition, uptake and, eventually, removal from the blood stream by the MPS. This occurs mostly in liver and spleen, which are the organs with a high abundancy of resident macrophages. These cells, belonging to the body immune system, act as filters removing particulate from blood (noxious xenobiotic substances, cell debris and particulate substances in general, including systemically administered nanoparticles). Significant amounts of nanoparticles are generally uptaken by the hepatic Kupffer cells (often over 70% of the injected dose), followed by splenic macrophages.

The largest majority of the strategies so far proposed to reduce nanoparticle uptake by MPS is focused on modifying the nanoparticle surface with polymer chains that could generate a steric hindrance with the macrophage membrane. PEGylation is certainly one of the most popular strategies whereby chains of polyethylene glycol (PEG) are either covalently or non-covalently attached or amalgamated on the nanoparticle surface. PEG has only partially solved the issue. In addition, and most importantly, the exposure to dietary products containing PEG is increasing the percentage of individuals developing antibodies against PEG, thus reducing its stealth potential.

An alternative strategy developed by the Inventors of the instant application is based on tuning the deformability of nanoparticles. With this aim Discoidal Polimeric Nanoconstructs (DPNs) with tunable stiffness have been designed. Preliminary studies revealed that rigid DPNs are particularly suitable for lung delivery but their circulation half-life is relatively short. Conversely soft DPNs are more suitable for tumor targeting and possess extended circulation time as demonstrated in a preclinical model of cancer therapy. The extended circulation time depends on the reduced recognition by macrophages which always sense the surrounding environment to snag pathogens and debris and are in general more prone to internalize stiff materials. Nonetheless, not all kind of drug delivery platform could be designed with tunable stiffness.

An alternative to tuning particle deformability is to administer specific pretreatments before the inoculation of the nanoparticles that carry a therapeutic agents and/or and imaging agent for the treatment and/or detection of a disease ("Secondary Administered Nanoparticles").

The aim of these pretreatments consist in transiently and reversibly reducing the phagocytic ability of macrophages, specifically residing in the liver and spleen. In this context, Gadolinium Chloride has been used as such a pretreatment. However, this compound is toxic and actually induce immune cell depletion rather than just inhibition. Gadolinium ions kills macrophages and other cells, as well. As such, the administration of this compound for this purpose is currently considered not feasible due to its effect on physiological functions and its intrinsic toxicity.

Also, studies are available on the possible use of glycine. However, it was never documented its use for improving the in-vivo performance of nanomedicines and, more importantly, the actual effect of this amino acid on macrophages is still disputed.

The administration of empty vectors is another investigated strategy; the strive of deviating drug loaded particles from ending up into liver macrophages in this case is based on stuffing resident macrophages using empty vector or reducing circulating opsonins. Commonly empty vector used are liposomes of diverse nature whose aim is to subtract opsonins from blood and/or physically fill these cells of particulate in order to avoid the uptake of other particulate secondarily administered (Secondary Administered Nanoparticles). The scientific publication Sun et al., (2017) "Improved tumor uptake by optimizing liposome based RES blockade strategy" *Theranostics* (2017), 319-328 discloses the effect of liposome administration in inhibiting the reticuloendothelial system (RES) clearance. The effects of the inhibition achieved by the liposome administration are temporary and reversible, and depend on the nature and amounts of lipids. In any case, the metabolism of these liposomes takes some time, the cell homeostasis is often restored over a long time frame and this administration could also result in macrophage activation. No active compound is used and no direct effect on phagocytic mechanisms is stroked.

In view of these premises, it is of considerable interest to identify new products or compositions that can have an immunomodulatory effect on macrophages achieving an improved transient inhibition of their phagocytic capacity. These product could be particularly useful, for example, i) to enhance accumulation of nanoparticles carrying active principles or a imaging agents secondarily administered (Secondary Administered Nanoparticles) within targeted pathological tissues and also ii) to be used in the treatment of diseases wherein an immunomodulatory effect on macrophages is desired (with consequent decrease in the phagocytic capacity).

SUMMARY OF THE INVENTION

The object of the present description is to provide nanoparticles comprising natural compounds designed to transiently and reversibly modulate the uptake function of Kupffer cells and other macrophages.

In accordance with the invention, the above object is achieved by means of the solution recalled specifically in the annexed claims, which constitute an integral part of the present description.

The present description provides nanoparticles comprising methyl palmitate (MP) and at least one serum globular protein.

The at least one serum protein may be selected in the group consisting of albumin, plasmin, transferrin, hemoglobin, ferritin, more preferably albumin.

In one or more embodiments, the nanoparticles consist of methyl palmitate (MP) and at least one serum globular protein, preferably selected in the group consisting of albumin, plasmin, transferrin, hemoglobin, ferritin, more preferably albumin.

In one or more embodiments, the nanoparticles herein disclosed may have an average diameter size comprised between 180 nm and 240 nm, preferably between 200 nm and 220 nm. The average diameter size has been measured by dynamic light scattering (DLS).

A method for producing the nanoparticles herein disclosed is also provided.

Moreover, the present description also provides compositions comprising nanoparticles and uses thereof.

The nanoparticles herein disclosed allows improving the biodistribution of active principles or imaging agents contained in particles secondarily administered toward the target tissue.

The nanoparticles are also effective in the treatment of diseases wherein macrophage activity could potentially hamper tissue integrity and/or alter tissue functionality. In one or more embodiments, the diseases may be selected in the group consisting of acute or chronic inflammation, scar formation, generation of fibrotic tissue, transplant rejection, atherosclerosis, cancer, wound healing, preferably scar formation and generation of fibrotic tissue.

The biocompatible nanoparticles disclosed in the instant application are able to transiently and reversibly act on the macrophage's phagocytic mechanisms without the need to resort to surfactant and/or cytotoxic substances.

BRIEF DESCRIPTION OF DRAWINGS

The invention will now be described in detail, by way of illustrative and non-limiting example only, with reference to the attached drawings, in which.

DETAILED DESCRIPTION OF THE INVENTION

Figure 1:
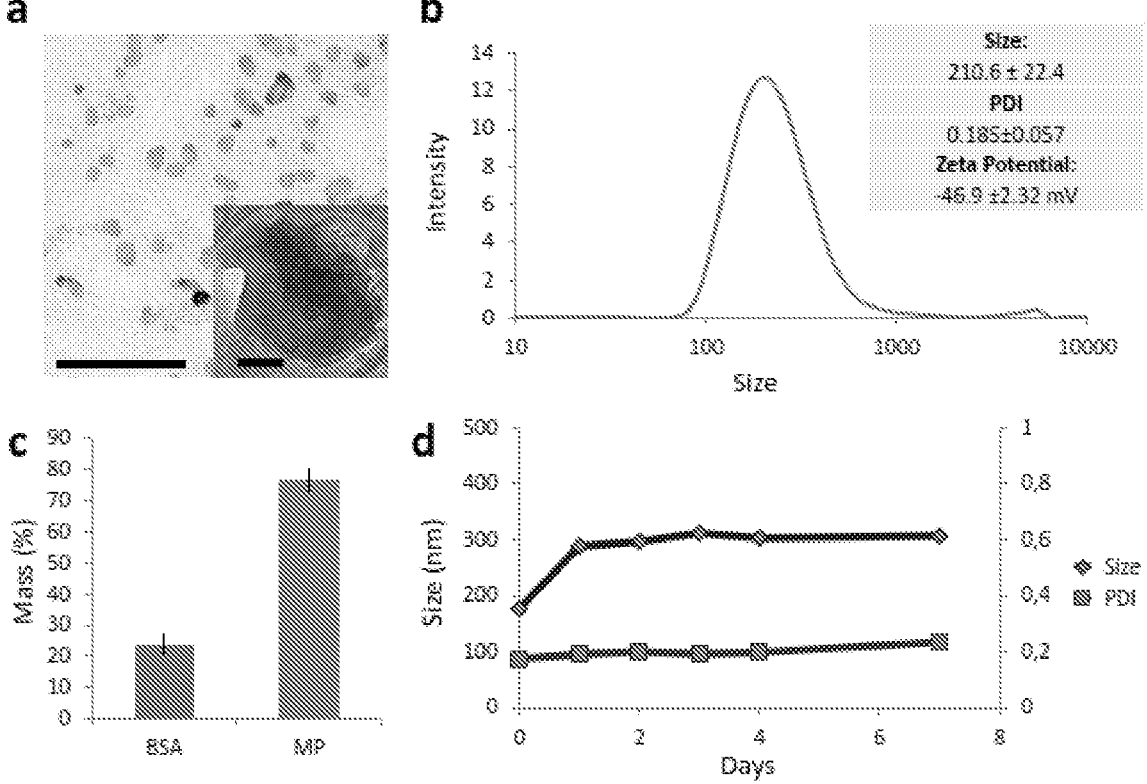
FIG. 1: Particles Characterization; a. TEM image of nanoparticles comprising methyl palmitate (MPNs); CryoEM of one single particle (scale bar: 1 μm and 100 nm in the inset). b. Dynamic light scattering (DLS) and Z-potential analysis of particles. c. Nanoparticles (MPNs) comprising methyl palmitate (MP) and bovine serum albumin (BSA) relative mass composition. d. 7 Days Stability Analysis in phosphate-buffered saline (PBS; size: solid line with rhombuses; polydispersion index (PDI): solid line with square).

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

The expressions "Secondary Administered Nanoparticles" or "secondary nanoparticles" or "Secondary Administered nanoparticles" (SAn) throughout the description refers to nanoparticles—carrying an active agent or an imaging agent—administered secondarily, i.e. after a pretreatment. In the context of the instant disclosure, Secondary Administered Nanoparticles are administered after or simultaneously to the administration of the nanoparticles (MPNs) object of the instant disclosure.

An embodiment of the present disclosure provides nanoparticles comprising methyl palmitate (MP) and at least one serum globular protein.

The at least one serum globular protein may be selected in the group consisting of albumin, plasmin, transferrin, hemoglobin, ferritin, more preferably albumin.

In one or more embodiments, the nanoparticles have an average diameter size comprised between 180 nm and 240 nm, preferably between 200 nm and 220 nm, as measured by dynamic light scattering.

In one ore or more embodiments, the nanoparticles comprises methyl palmitate and at least one serum globular protein, preferably albumin, in a weight ratio (w/w) comprised between 5:1 and 2:1, preferably 3:1.

Under optimal conditions, the relative masses of the two particle components may be equal to 76.49%±3.55 of methyl palmitate and 23.50±3.55% of serum albumin, which corresponds to about 3:1 ratio.

In one or more embodiments, the nanoparticles consist of methyl palmitate (MP) and at least one serum globular protein, preferably selected in the group consisting of albumin, plasmin, transferrin, hemoglobin, ferritin, more preferably albumin.

The present description also provides a method for producing the nanoparticles herein disclosed, the method comprising the following steps:

preparing a first solution comprising methyl palmitate,
  preparing a second solution comprising at least one serum globular protein, preferably selected in the group consisting of albumin, plasmin, transferrin, hemoglobin, ferritin, more preferably albumin,
  adding the second solution to the first solution to obtain a third solution comprising methyl palmitate and the at least one serum globular protein in a weight ratio (w/w) comprised between 2:2.5 and 2:20, preferably between 2:5 and 2:10,
  mixing the third solution thereby allowing the production of nanoparticles in the mixed third solution,
  separating the nanoparticles.

In one or more embodiments, the mixing step may be carried out by sonication, preferably for a period of time comprised between 0.5 minutes and 3 minutes.

In one or more embodiments, the first solution may be an alcoholic solution prepared by dissolving methyl palmitate in absolute ethanol, preferably in a weight ratio (w/w) of 1:1.

The second solution may be a solution comprising at least one serum globular proteins, such as albumin, plasmin, transferrin, hemoglobin, ferritin, more preferably albumin, dissolved in phosphate-buffered saline (PBS), preferably in an amount of 50 mg/ml.

In one or more embodiments, the method may further comprise at least one step of washing the nanoparticles formed upon mixing the first solution and the second solution to remove un-complexed proteins. The washing step may be carried out by using a buffer as washing solution, for example phosphate-buffered saline (PBS).

In one or more embodiments, the separating step may be carried out by concentrating the nanoparticles to obtain a concentrate containing the nanoparticles.

The separating step may be carried out by at least one centrifugation cycle of the solution containing the nanoparticles with a rpm value comprised between 13,000 and 15,000 rpm.

The at least one centrifugation cycle can be carried out for a period of time comprised between 50 minutes and 90 minutes.

The separation step, preferably carried out by centrifugation, may be carried out at a temperature comprised between 4° C. and 9° C.

The resulting nanoparticles are stable nanoparticles produced through a self-assembly method.

The method herein disclosed is very simple and safe and has the advantage of an easy production scale up; biocompatible reagents only are used in the different steps. Surfactants and cytotoxic substances are not required and the final product is free of any harmful chemical compound. The obtained particles are completely biocompatible, biodegradable, non-toxic, and cleared by the body.

Particles obtained by the method disclosed in the instant application are stable for 7 days at 25° C. They can also be stored at 4° C. for a period of at least 30 days.

The present disclosure also provides a composition comprising one or more nanoparticles.

The nanoparticles and the compositions comprising the nanoparticles herein disclosed may further comprise pharmaceutically acceptable buffers, diluents, excipients, adjuvants, and/or carriers.

The composition comprising the nanoparticles may also be made, for example, in the form of a cream, ointment, gel, suspension suitable for administration by injection or spray, or as a lyophilized product for reconstitution before use with water or other suitable vehicles.

Such compositions comprising the nanoparticles may contain excipients and/or carriers suitable for the chosen route of administration such as preservatives, thickeners, antioxidants, emollients, moisturizers, natural or artificial fragrances, surfactants.

The nanoparticles and/or the compositions comprising the nanoparticles herein disclosed may be used in increasing the bioavailability of an active agent or of an imaging agent in a mammal, wherein said nanoparticles or said composition comprising the nanoparticles are adapted to be administrated before the administration of the at least one active principle or the at least one imaging agent, wherein said active principle or said imaging agent are carried by at least one Secondary Administered Nanoparticle.

The disclosure also provides combined preparations comprising the nanoparticles herein disclosed and at least one active principle or at least one imaging agent, said at least one active principle or said at least one imaging agent being contained in at least one Secondary Administered Nanoparticle, for separate and sequential use in inhibiting the phagocytic activity of the macrophages and in increasing the bioavailability of said active principle and/or said imaging agent in a mammal.

As will be shown in the next sections, the nanoparticles (MPNs) herein disclosed—comprising methyl palmitate (MP)—are capable to transiently and safely inhibit the phagocytic activity of Kupffer cells and other macrophages. The transient inhibition of the cell phagocytic activity upon administration, preferably by intravenous administration, of MPNs diverts particles carrying an active agent or an imaging agent (Secondary Administered Nanoparticles) from the liver to the actual biological target—the pathological tissue (cancerous lesion, vascular plaque, blood clot, edematous tissue, inflamed tissue, and so on).

A portion of MPNs accumulates in the Kupffer cells of the liver. Here, they can rapidly exert their inhibitory activity on the resident macrophages. MPNs act reversibly on the α-tubulin protein of macrophages. This limits the avidity of macrophages preventing the uptake of secondary administered nanoparticles which can then circulate longer and eventually reach in a higher number the pathological tissue. This effect is transient and full reversible between 12-24 h post MPNs treatment. During this time frame, circulating Secondary Administered nanoparticles are significantly less affected by MPS and thus their accumulation to the biological target can be enhanced.

It is important to highlight the reversibility of the process, since a permanent inhibition would lead to an immunologic paralysis, exposing patients to pathogens over a long period of time.

The nanoparticles herein disclosed, therefore, would apply and enhance the performance of any Secondary Administered Nanoparticles. Indeed, MPNs have been tested in conjunction with a broad variety of Secondary Administered Nanoparticles, causing a temporary inhibition of Mononuclear Phagocytic System. Evidence of a significant decrease in the sequestration activity of macrophages will be shown in the next sections.

The results of in vivo tests are also provided in the following, conducted on rigid particles designed as Secondary Administered Nanoparticles for carrying an active agent or an imaging agent and for lung delivery, which heavily accumulate in the liver. The experiments reveals that the preliminary MPNs treatment is capable of reducing hepatic accumulation of such rigid particles as well as enhancing their natural tropism for the lungs. This means that the Secondary Administered Nanoparticles (rigid particles in this case) would be less uptaken by resident macrophages, thus circulate longer and accumulate more within their natural targeted organ (lungs in this case).

To date, no treatment is capable to achieve this result without inducing significant toxicity or acting on specific mechanisms.

The inhibition of the macrophage's phagocytic activity may be preparatory for subsequent systemic administration of active principles or imaging agent, for example contained in particles (nanomedicine). In such way, the active principles accumulate preferentially at the pathological site, in that their non-specific accumulation within the liver is inhibited; specifically, the phagocytic ability of macrophages is recovered while the particles containing the active principle or the imaging agent are already lodged within the pathological tissue.

The description thus provides a method for increasing the bioavailability of an active principle and/or of a imaging agent in a subject, the method comprising the steps of:

administering the nanoparticles comprising methyl palmitate and at least one globular serum protein, preferably albumin, or a composition comprising the same, administering the active principle and/or a imaging agent, wherein the active principle and the imaging agent are contained in at least one Secondary Administered Nanoparticle.

The treatment may preferably follow the following time line:

Time 0 h: MPNs Administration (pretreatment)

Time 5 h-16 h: Administration of the active principle and/or a imaging agent. The pretreatment time may vary based on the features of the Secondary Administered Particles.

The main advantages of the technical solution herein disclosed resides in: i) the use of nanoparticles that partially accumulates in Kupffer cells; ii) the transient effect exerted by the nanoparticles on macrophages allowing this cell population to be temporary interdicted to exert their main function instead of being depleted from the body; iii) the use of a complexed product resulting from the formulation of an endogenous protein carrier, preferably albumin, with an immunomodulatory lipid.

The nanoparticles and the compositions including the nanoparticles object of the present description may also be used as a pharmaceutical composition whenever the reduction of macrophage's phagocytic activity is required.

In one or more embodiments, the nanoparticles and the compositions comprising nanoparticles herein disclosed may be used for reducing the macrophage's phagocytic activity.

The nanoparticles herein disclosed are effective in the treatment of conditions in which macrophage activity may hamper tissue integrity or alter tissue functionality.

In one or more embodiments, such conditions may be selected in the group consisting of acute or chronic inflammation, scar formation, generation of fibrotic tissue, transplant rejection, atherosclerosis, cancer, wound healing.

In one or more embodiments, the compositions comprising nanoparticles object of the present description may find application also as cosmetic composition, for example for the prevention and treatment of scars.

EXAMPLES

Methyl Palmitate Nanoparticle Production Method 2 mg of methyl palmitate (Sigma-Aldrich) is premixed 1:1 (w/w) with absolute ethanol to achieve a first solution.

100 μl of a 50 mg/ml serum albumin (BSA) (Sigma-Aldrich) solution (second solution) are added to 2 mg of methyl palmitate dissolved in ethanol (first solution) in a 1.5 ml eppendorf tube obtaining a third solution.

It is possible to generate nanoparticles also using different serum albumin masses. Specifically, for a fixed mass of MP equal to 2 mg, particles were generated using a serum albumin mass ranging between 2.5 mg and 20 mg. The optimal mass range was identified to be within 5 mg and 10 mg.

The third solution is mixed by sonication into a water bath at maximum power for 3 min. Nanoparticles start forming within the first 10 seconds and the mixed third solution starts appearing turbid.

Then, nanoparticles are washed twice with 1 ml of phosphate-buffered saline (PBS) and separated. Specifically, the nanoparticles are separated by centrifugation at 12,700 RPM for 1 h at 4° C.

For in vivo studies 3× batches were obtained by linearly scaling up masses and volumes of the reagents and following the same procedures described above.

In order to characterize the final mass of the injected dose, serum albumin and methyl palmitate were quantified after separation.

Results obtained have shown the following nanoparticles mass ratio: the nanoparticles are constituted by 76.49%±3.55 of methyl palmitate and 23.50±3.55% of bovine serum albumin.

A dynamic light scattering (DLS) analysis of the nanoparticles, via a Zetasizer Malvern, revealed a diameter of about 180 nm, a polydispersion index of 0.182, a surface electrostatic charge of −46.9±2.32 mV. MPNs are stable at 37° C. for 9 days, despite a slight increase in size retrieved at 24 h.

MPNs are easily uptaken by macrophages and reveal a spherical shape.

A monodisperse MPNs composition is used to transiently and reversibly modulate the uptake function of Kupffer cells, improving the biodistribution of particles designed for carrying an active agent or an imaging agent toward a target tissue (Secondary Administered Nanoparticles), and thus affecting efficacy of such Secondary Administered Nanoparticles. The use of a monodisperse population of nanoparticles may optimize the inhibitory activity of MP on macrophages.

Particles Characterization

Methyl Palmitate nanoparticles (MPNs) were analyzed at TEM (FIG. 1a). It is possible to appreciate spheroidal nanoparticles of uniform dimension. CryoEM analysis (FIG. 1a-inset) shows particle naïve shape in solution in high magnification. The analysis confirmed the spheroidal shape of the nanoparticles and revealed the non-uniform density of constituents within its body, suggesting that methyl palmitate holds together different protein components. DLS analysis reported in FIG. 1b shows that particles dimension is about 210 nm with a polydispersion index (PDI) of 0.185±0.057 and that MPNs surface charge is equal to −46.9±2.32. The mass ratio of the two compounds constituting MPNs (methyl palmitate and serum albumin) was quantified by gas chromatography coupled to mass spectrometry for methyl palmitate and BCA assay for serum albumin. Results indicate the nanoparticles are constituted by 76.49%±3.55 of methyl palmitate and of 23.50%±3.55 of serum albumin (FIG. 1c).

Particles are stable for 4 days in PBS at 37° C. as shown in FIG. 1d. A slight size increase was documented at day 2, the PDI stayed stable over time.

Figure 2:
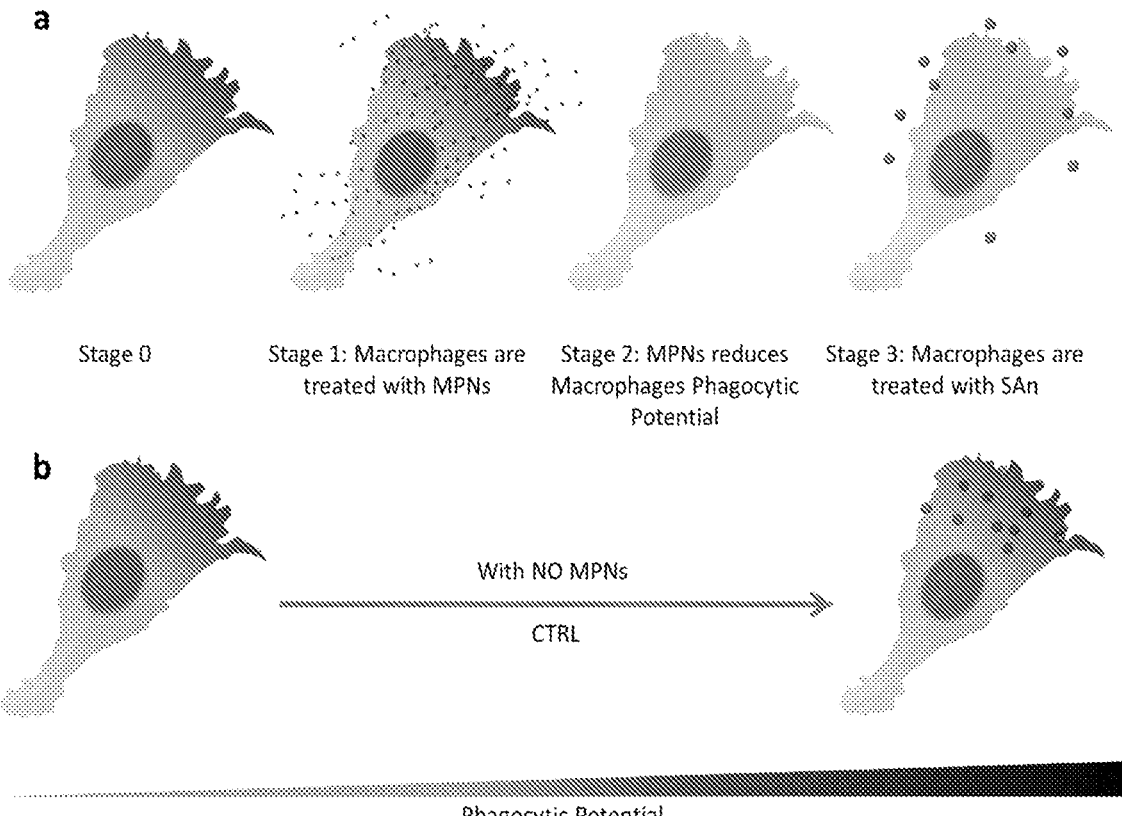
FIG. 2: Schematic representation of macrophages treated with nanoparticles. a. Macrophages are first exposed to methyl palmitate (MP) and serum albumin nanoparticles (MPNs), then to Secondary Administered nanoparticles (SAn). b. Macrophages treated only with SAn, without any pretreatment with MPNs.

Internalization of Secondary Administered Nanoparticles in BMDM Treated with MPNs Nanoparticles Flow Cytometry The ability of MPNs to efficaciously inhibit the internalization of Secondary Administered nanoparticles (SAn) was tested in Bone Marrow Derived Monocytes (BMDM). A schematic of the experiment is shown in FIG. 2 reporting a representation of macrophages treated or not with MPNs.

Macrophages pretreated with MPNs tend to internalize Secondary Administered nanoparticles at a minor extent with respect to untreated ones. Secondary Administered nanoparticles are all those particles that carry a therapeutic agents and/or and imaging agent for the treatment and/or detection of a disease. Examples of clinically approved secondary nanoparticles are Doxil and Myocet (liposomes loaded with the anti-cancer drug doxorubicin); DaunoXome (liposomes loaded with the anti-cancer drug daunorubicin); Margibo (liposomes loaded with the anti-cancer drug vincristine); and Genexol PM and Nanoxel M (micelles loaded with paclitaxel); Abraxane (serum proteins mixed with paclitaxel); iron oxide nanoparticles for MR imaging.

As a proof of concept, the secondary nanoparticles tested in the study reported in the instant disclosure were the following: 750 nm and 200 nm Polystyrene Particles (P750 and P200), 2 µm rigid Discoidal Polymeric Particles (rDPNs), 200 nm Spherical Polymeric Particles (SPNs). P750 and P200 particles are spherical fluorescently labeled polystyrene particles commercially available. rDPNs and SPNs are fluorescently labeled polymeric nanoparticles mainly constituted by PLGA. Both particles are fabricated by the Inventors of the instant application following known different procedures. The major difference among these two nanoparticles is their geometry since the first ones are 1,000 nm discoids while the second ones are 200 nm spheres.

Secondary Administered Nanoparticles were administered according to their internalization time frames which were estimated in previous experiments. Bigger particle treatments were performed administering the nanoparticles of the instant disclosure (MPNs) and Secondary Administrated Nanoparticles (SAn) at the same time. Secondary Administrated Nanoparticles—P200 and SPNs—were administered after an overnight pretreatment with MPNs and for 90' and 30' respectively.

Figure 3:
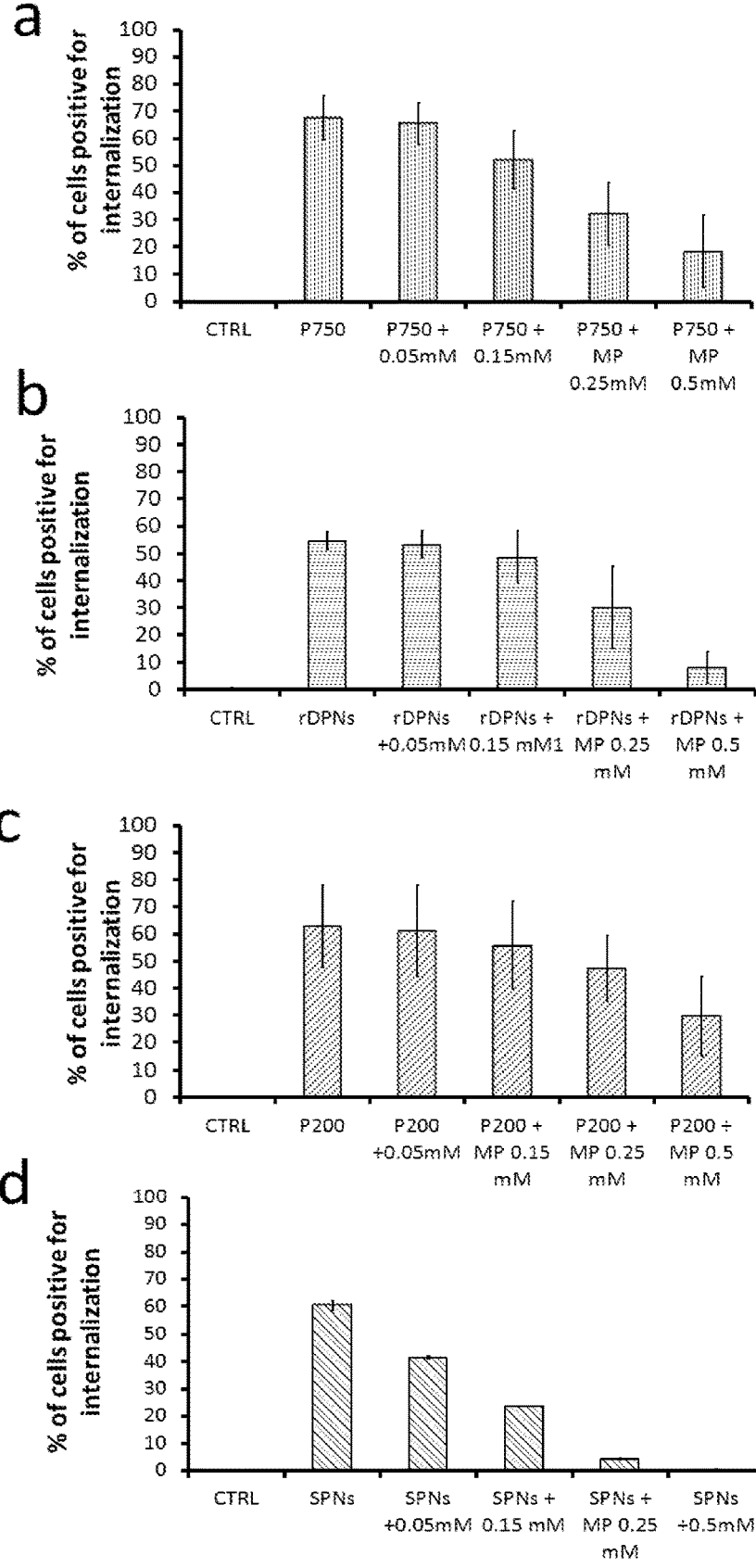
FIG. 3: Flow cytometry analysis of the inhibition of secondarily administered nanoparticles internalization in Bone Marrow Derived Monocytes (BMDM) after overnight (O.N.) MPNs treatment (different dosing were tested). a. Internalization of 750 nm polystyrene beads (P750; incubation time: overnight); b. Internalization of 2 μm rigid Discoidal Polymeric Particles (rDPNs; incubation time: overnight); c. Internalization of 200 nm Polystyrene beads (P200; incubation time: 1 h 30 minutes); d. Internalization of Spherical Polymeric Particles (SPNs; incubation time: 30 minutes).

In FIG. 3, the inhibitory effect of the nanoparticles herein disclosed on the Secondary Administered Nanoparticles internalization in BMDM is shown. It is possible to appreciate that increasing MP amount (which follows the molarity increase of MP) the percent amount of positive cells decreases in a dose dependent fashion. The same trend was retrieved for all the Secondary Administered Nanoparticles.

In particular, in FIG. 3a it is possible to appreciate that the percent amount of cells positive for internalization of P750 is half reduced using a dose of MPNs equal to 0.25 mM with respect to untreated cells. More in details, the percent of positive cells moves from 67.4% of untreated cells to 32.15% of cells treated with 0.25 mM of MPNs.

Similarly for the Secondary Administered Nanoparticles rDPNs (FIG. 3b) a dose equal to 0.25 mM of MP is able to reduce nearly by half the percent of positive cells, moving from 54.77% of untreated cells to 30.17% of treated cells.

BMDM were treated with SPNs and P200 for shorter time frames as mentioned. In these experiments BMDM were pretreated with MPNs, similar results were found. The percent of cells positive for P200 internalization moved from 62.83% of the control condition to 47.31 of 0.25 mM condition (FIG. 3c).

For SPNs the difference between the untreated cells and the cells treated with 0.25 mM of MP is even more marked. Percent of cells positive for internalization moves from 60.4% to 4.35% (FIG. 3d).

For all of the Secondary Administered Nanoparticles considered, all the conditions in between show a progressive decrease of the percent of cells positive for internalization in response to an increase of MP concentration. Cells treated with the only higher concentration considered (0.5 mM) still follow this trend, showing a further inhibition of secondary particles internalization.

In details, treating BMDM with 0.5 mM of MPNs the percent of positive cells for internalization moves from 67.4% to 18.45% for P750, from 54.77% to 8.12% for rDPNs, from 62.8% to 29.83% for P200 and from 60.4% to 0.75% for SPNs.

The 0.25 mM condition were considered as reference condition since it seems to be sufficiently effective to guarantee a discrete inhibition in all the tested Secondary Administered Nanoparticles and compatible with cell physiology. For this reason, this dosing was used for further analysis. Further experiments were performed using nanoparticles comprising methyl palmitate and Fetal Bovine Serum (FBS).

Figure 4:
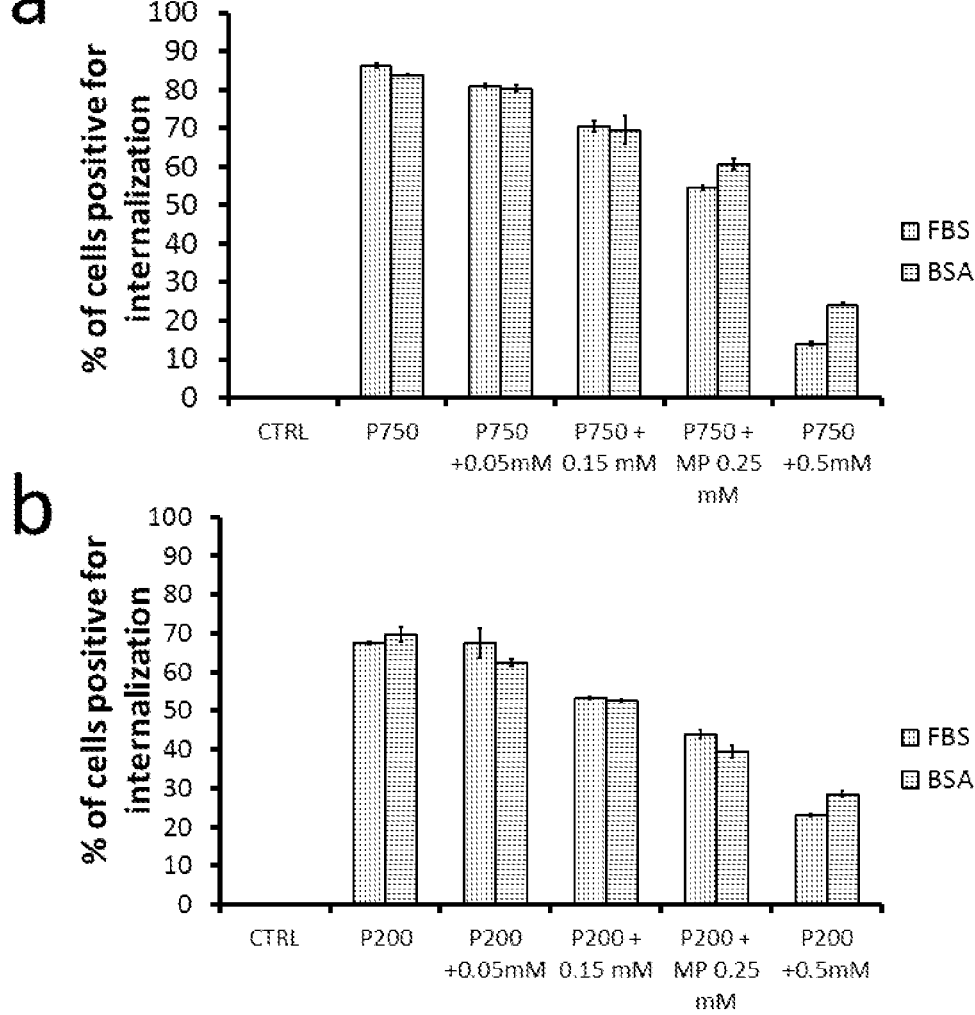
FIG. 4: Comparison between fetal bovine serum (FBS) and bovine serum albumin (BSA) MPNs formulation on the inhibition of 750 nm polystyrene beads internalization (P750) and 200 nm polystyrene beads (P200) respectively.

In order to demonstrate that formulations prepared by using methyl palmitate and Bovine Serum Albumin exert the similar effects, the same experiment proposed in FIG. 3 was replicated using MPNs fabricated with FBS and with BSA (FIGS. 4a and 4b). The two treatments resulted to be sufficiently similar to each other and led to conclude that the active compound (methyl palmitate) acts similarly when complexed with FBS or BSA.

Confocal Microscopy

Figure 5:
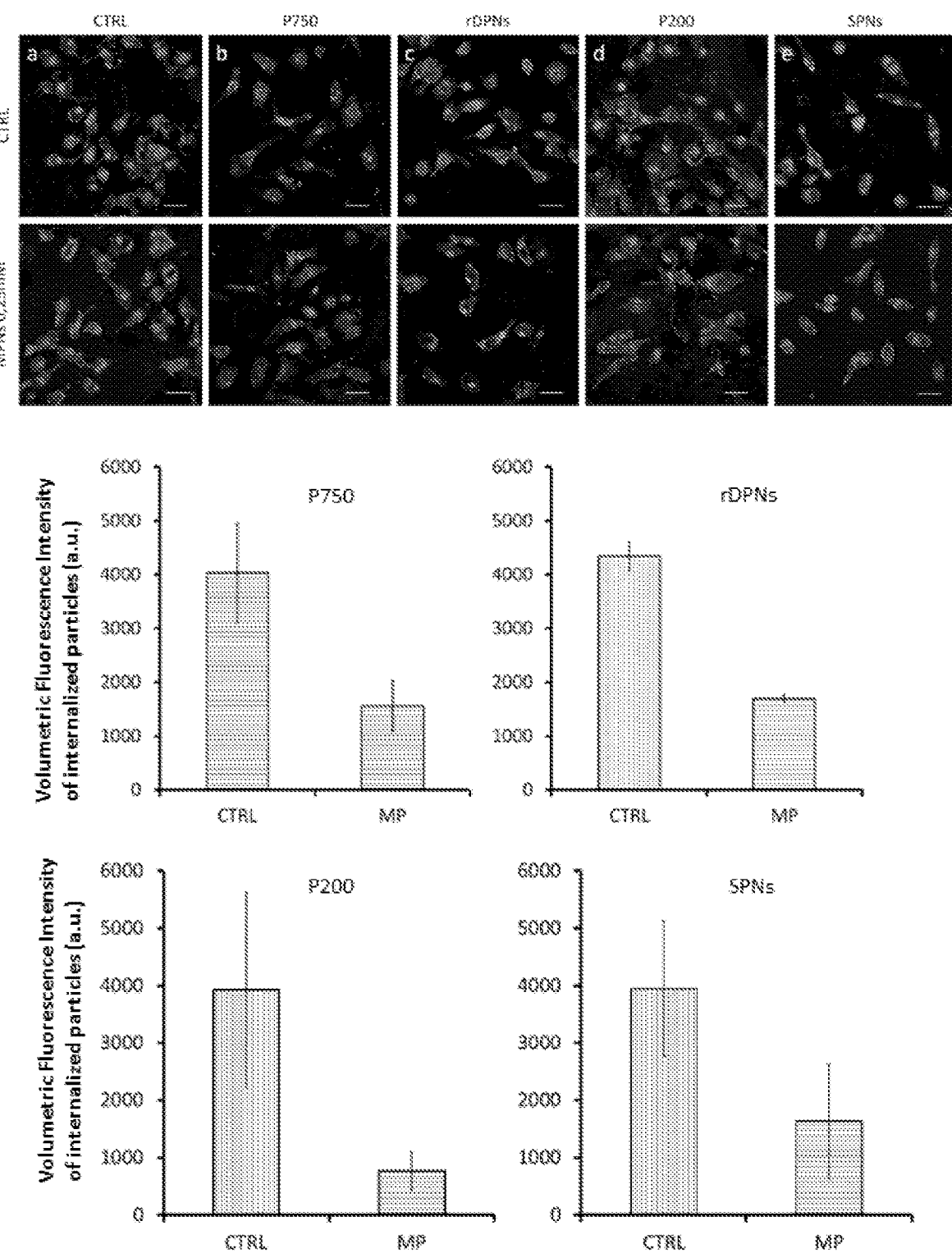
FIG. 5: Confocal imaging and relative statistical analysis of the inhibition of SAn internalization in BMDM after overnight MPN treatment. a) Control; b) 750 nm polystyrene beads (P750) (incubation time: overnight); c) rigid Discoidal Polymeric Particles (rDPNs) (incubation time: overnight); d) 200 nm polystyrene beads (P200) (incubation time: 1 h 30 min); e) 200 nm SPNs (SPNs) (incubation time: 30 min). Plasma membrane staining was performed using Wheat Germ Agglutinin, nuclei staining using DAPI; P750 and rDPNs appear as high intense circular spots. P200 appears as less intense small spots and SPNs as high intense small spots. Scale bar=20 μm. Histograms represent the fluorescence intensity of internalized particles (SAn).

MPNs treatment effect on Secondary Administered Particles internalization was also measured by confocal microscopy as shown in FIG. 5. Wheat germ agglutinin (WGA) staining of glycosylic residue of membrane proteins highlight plasma membrane, this staining is useful to define cells edges and thus is effective in understanding if a particle can be considered as inside the cell body; nuclei were stained using DAPI. In this experiment control condition (5a) refers to untreated cells and the same Secondary Administered Nanoparticles used for the flow cytometry test were taken in account: P750 (5b), rDPNs (5c), P200 (5d), and SPNs (5e). Images were acquired in z-stack in order to consider in the analysis particles occupying the entire cell volume.

Representative maximum intensity projection images show the reduced amount of Secondary Administered Nanoparticles retrieved inside the BMDM in the MPNs treated condition with respect to untreated cells. It is possible to appreciate the reduction of the internalization rate for all the Secondary Administered Nanoparticles administered when pretreating with MPNs occurs. The plots reports the quantification of internalized Secondary Administered Nanoparticles fluorescence intensity. This parameter was measured in the entire volume of the cell. No macroscopic visible alteration of plasma membrane structure was found.

Molecular Mechanisms and Reversibility

Confocal Microscopy

In order to understand how the internalization inhibitory effect is exerted, some analysis were performed on microtubules polymerization. Microtubules were stained by using a monoclonal anti-$\alpha$-tubulin antibody (Sigma; T5168) and a fluorescently labelled secondary antibody (Abcam; ab6786).

Figure 6:
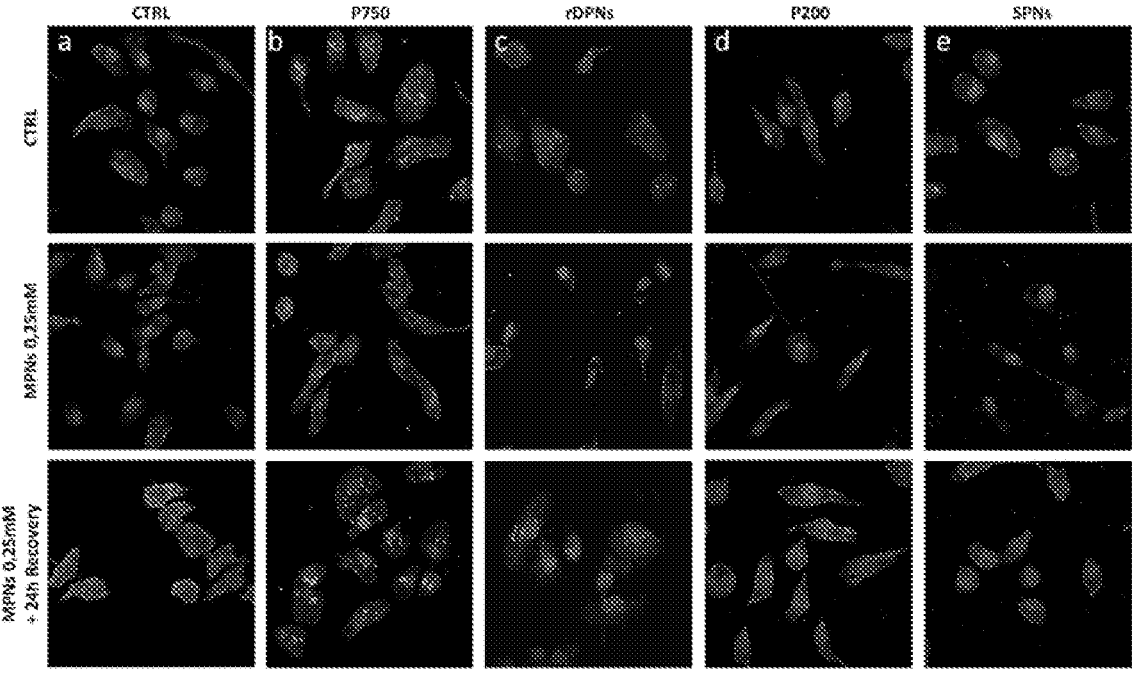
FIG. 6: α-tubulin immunostaining of BMDM. First row: untreated cells; second raw: cells treated with 0.25 mM of MPNs; third raw: cells treated with 0.25 mM MPNs which underwent 24 h recovery before being treated with SAn. As SAn, the following list of nanoparticles were used: a. no SAn; b. P750; c. rDPNs; d. P200; e. SPNs. The images show the mechanism of action of MPNs which is based on impairing microtubules polymerization. The reversibility of the treatment can be appreciated in the images of the third raw where tubulin fibers start reassembling with consequent recovery of the phagocytic capability. In all images, nuclei were stained using DAPI; Particles appears in the image as spots of different intensity and size.

Images acquired in z-stack and presented in maximum intensity projection modality show that cells treated with the nanoparticles herein disclosed MPNs lose partially the architecture of microtubules (FIG. 6); this consideration applies also if exclusively MPNs are administered (FIG. 6a). The loss of the microtubules architecture is associated to a reduced uptake of Secondary Administered Nanoparticles (reported above). This phenomenon is also evident from the images in FIG. 6 where the same Secondary Administered Nanoparticles of previous experiments were administered according to the same conditions above described: P750

(6b), rDPNs (6c), P200 (6d) and SPNs (6e). In the controls, it is possible to appreciate regular $\alpha$-tubulin structures forming microtubules, these structures in most of the cases start from a centromere located in the proximity of cell nucleus.

In the second raw, BMDM treated with MPNs 0.25 mM are presented, cells show an altered conformation of microtubules architecture together with a reduced amount of particles within the cell body. Alterations found include: loss of microtubules centromere, disorganization of the regular structure of microtubules, presence of parallel $\alpha$-tubulin structure along cell edges and compartmentation of cell body areas. These findings apply equally to the entire population of analyzed cells. In summary, the data reveal that MPNs treated macrophages lose their phagocytic potential due to the impaired $\alpha$-tubulin polymerization. In FIG. 6 it is also reported the reversibility of this effect (third raw). Macrophages which were treated for 16 h with MPNs and which underwent a 24 h recovery period were again able to internalize Secondary Administered Nanoparticles. Together with the recovery of the phagocytic activity cells resolved the microtubules alterations previously found. The fact that as the microtubules recover they architecture the cells recover the capability to internalize Secondary Administered Nanoparticles, strengthen the hypothesis that MPNs effect on particles internalization is mediated by temporary alterations of $\alpha$-tubulin cycle.

Flow Cytometry

Figure 7:
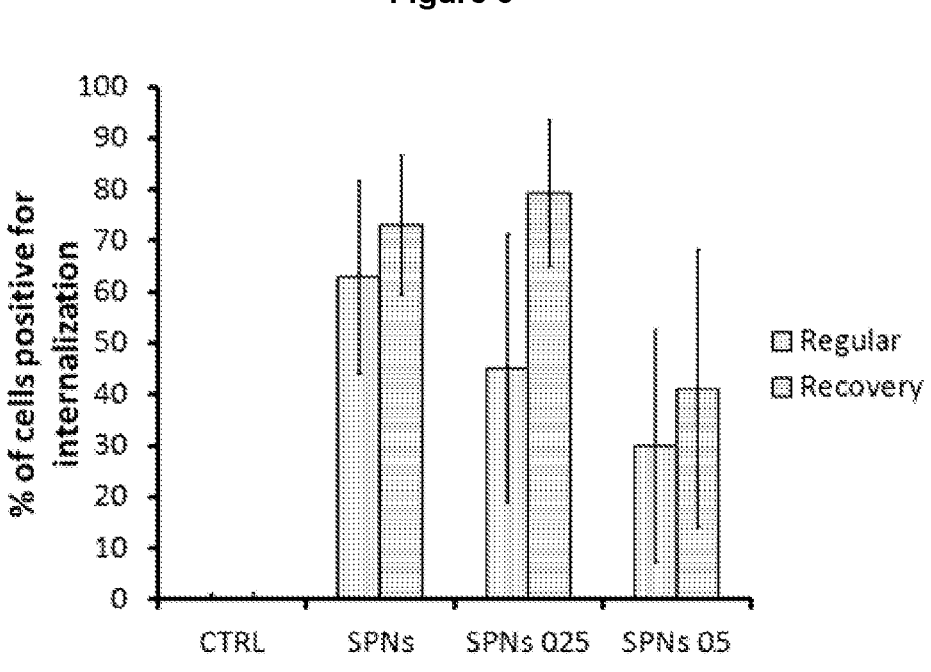
FIG. 7: Recovered phagocytic activity tested by flow cytometry. The bar chart presents the percent of cells positive for SPNs internalization in untreated cells (regular) and overnight MPNs stimulated cells after 24 h recovery.

The recovery of internalization capability was also monitored by Flow Cytometry using 2 different MPNs dosing (0.25 mM and 0.50 mM). In this experiment only one of the secondary particles previously considered was used (SPNs). As for $\alpha$-tubulin experiment the cells underwent an overnight treatment with MPNs followed by 24 h recovery. Secondary particles were than administered respecting the same timing (FIG. 7). Percent of cells positive for SPNs internalization for cells untreated and treated with MPNs were in line with previous findings indicated in the disclosure. Regarding the recovery of the phagocytic activity, data revealed a complete recover of this function for the 0.25 mM of MPNs condition. Cells treated with the higher dose considered (0.50 mM) recovered only partially the phagocytic capability, it cannot anyway exclude that at longer time point the recover occurs also using concentrations equal to 0.50 mM of MPNs.

Transmission Electron Microscopy (TEM)

Figure 8:
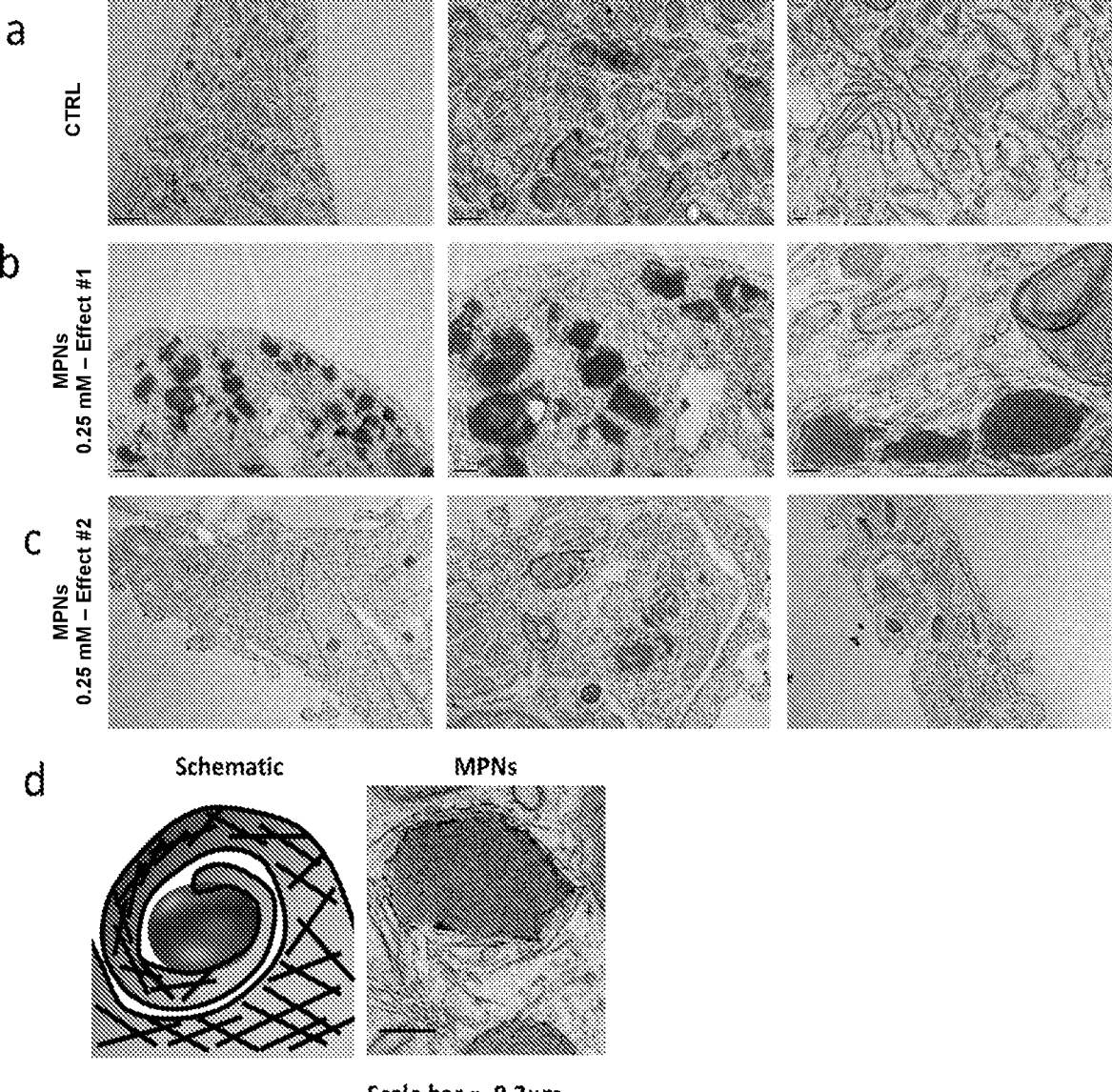
FIG. 8: TEM images of MPNs treated BMDMs. Cells possess some peculiar characteristics reported in figure as Effect #1 and #2. a. untreated BMDM (Ctrl). b. presence of lipids accumulation in structures that should be ascribed to vesicles—Effect #1. These vesicles are presented as wrapped into segmented spiral formations as schematically indicated in d. (MP particles may be internalized through a mechanism involving cytoskeleton and microtubules, the tubulin present in the proximity of the particles get palmitoilated and subsequently anchored to the plasma membrane which surround it. Segmented spiral formations indicates membranes remaining straight and stiff after the α-tubulin anchoring. After tubulin palmitoilation the tubulin cycle is altered and the de-polymerization of microtubules is impaired as phagocytosis). c. the presence of peculiar straight lines—Effect #2. These lines could be membrane anchored tubulin which cannot be de-polymerized for until de-palmitoilation.

Imaging of BMDM which internalized MPNs was also performed using Transmission Electron Microscopy. BMDM cytoplasm appear to be very dense and as it is possible to appreciate in FIG. 8a. Once internalized, MPNs seems to aggregate into bigger structures often surrounded by segmented spiral structures presumably composed by membranes and microtubules (FIG. 8b). Cells undergoes some changes partially common to the ones found by confocal microscopy. Some peculiar straight lines appears (FIG. 8c), these lines resemble those retrieved when staining $\alpha$-tubulin is carried out by immunostaining. This phenomenon could be caused by tubulin palmitoilation and subsequent anchoring to the plasma membrane surrounding it. Tubulin palmitoilation is able to alter tubulin cycle impairing microtubules depolymerization. In FIG. 8d is presented a schematic of the interface between MPNs and cell. Particles is entrapped by the cell and internalized. As mentioned, MPNs accumulate in bigger structures whose higher magnification is presented in FIG. 8d. Due to their dark color these structures could be membranes attached to tubulin fibers due to tubulin palmitoilation.

Schematic of the Internalization Steps in Different Conditions

Figure 9:
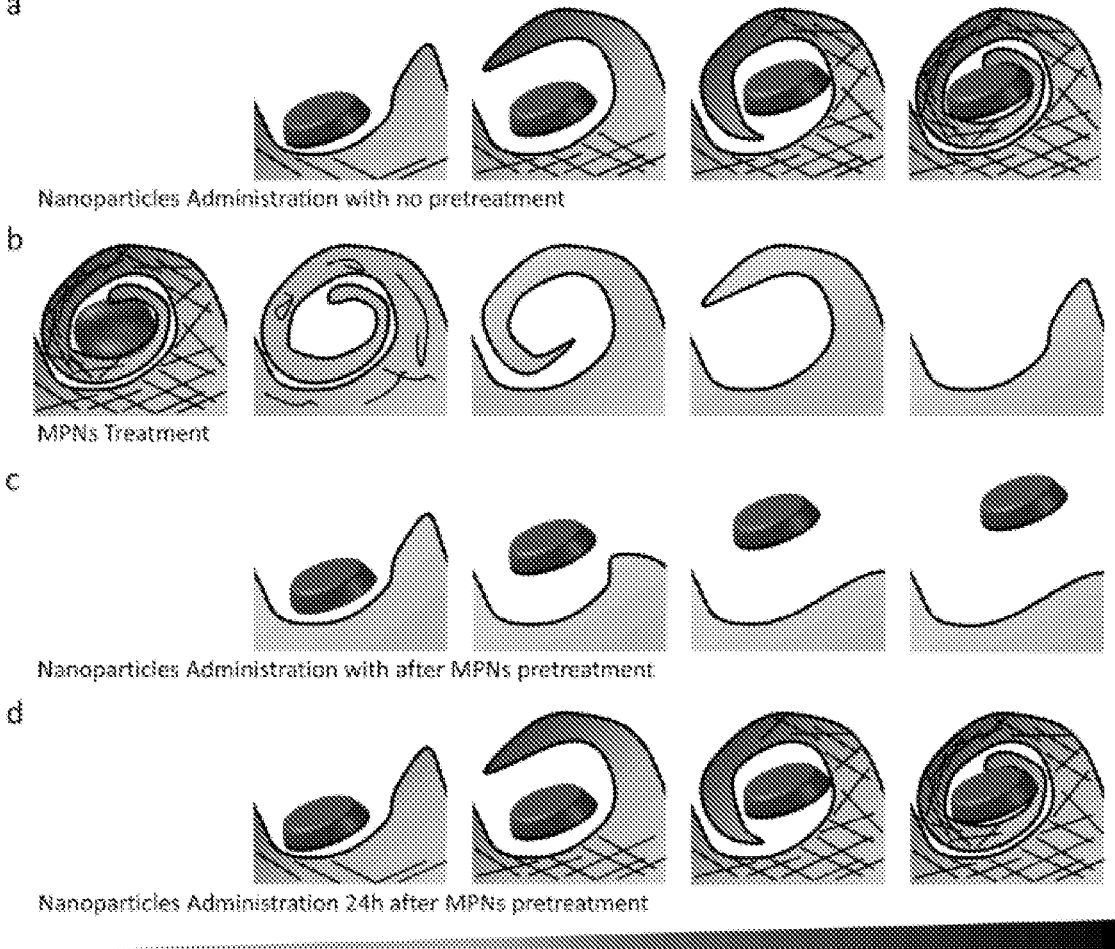
FIG. 9: Schematic representation of the different scenarios. a. events leading to nanoparticle internalization (Nanoparticles Administration with no Pretreatment); b.-c. inhibition of the phagocytic potential mediated by MPNs (MPNs treatment and Nanoparticles Administration after MPN pretreatment); d. recovered phagocytic capability occurring 24 h after MPNs treatment (Nanoparticles Administration 24 h after MPN Pretreatment).

In FIG. 9, a schematic of the phenomenon is proposed; nanoparticles internalization process take place thanks to microtubules mediated plasma membrane rearrangements (9a). FIG. 9b shows the uptake of a MPNs particle impairing microtubules rearrangements. FIG. 9c shows the escape of a Secondary Administered Nanoparticle administered in the time frame in which the cell is refractory to particles internalization. FIG. 9d shows the recovered capability of the cell to internalize particles after the refractory time frame. In this phase the capability to rearrange microtubules is recovered and allows the cell to internalize particles.

In Vivo Experiments

In order to prove the efficacy and the reversibility of the treatment with the nanoparticles herein disclosed, C57 Black mice (n=4-6) were pretreated with MPNs before administering 2 μm rDPNs particles. 2 μm rDPNs were chosen in order to investigate the capability of MPNs to influence their biodistribution by deviating a number of particles from liver (which heavily subtract this kind of particles from blood circle) to lungs (the district these particles are designed for, basing on shape and size features). 3 batches of MPNs were injected e.v. in one single bolus, the treatment with MPNs lasted 2 h or 4 h to prove the efficacy and 16 h to prove the reversibility.

Figure 10:
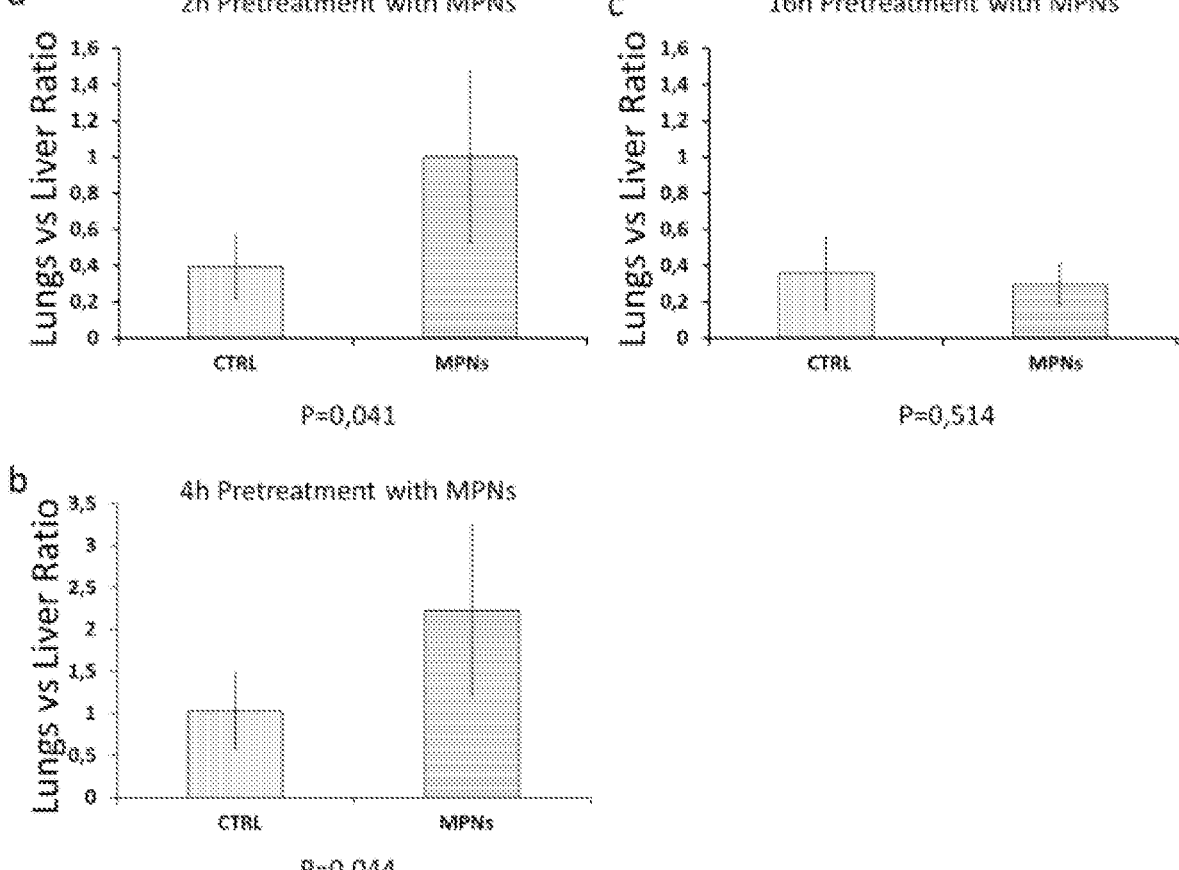
FIG. 10: Intravital Imaging System (IVIS) analyses. ex vivo rigid DPNs bio-distribution in healthy black mice treated or not with MPNs. The lung vs liver ratio was evaluated in black mice after 2 h (a), 4 h (b) and 16 h (c) pretreatment with MPNs and 2 h treatment with 2000 nm rDPNs.

Cy5 labelled 2 μm rDPNs were administered upon MPNs pretreatment and particle biodistribution was monitored using Intravital Imaging System (IVIS) (FIG. 10).

At 2 h and 4 h time points some of the animals were sacrificed and liver and lungs were analyzed at IVIS. Lung vs liver ratio distribution was calculated for all of the analyzed animals (FIG. 10).

The ratio reveals that after 2 h and 4 h pretreatments, MPNs are able to influence rDPNs biodistribution by reducing the number of rDPNs uptaken by the liver. This action is probably obtained by modulating Kupfer cells activity.

The reduced uptake in the liver district grants for a longer circulating time and favors rDPNs tropism for the lung district. The reversibility of the treatment is demonstrated by increasing the pretreatment time to 16 h.

In the animals which underwent 16 h pretreatment with MPNs, no significant difference was shown in the ratio lungs vs livers.

This finding demonstrates that the frame of action of MPNs is relatively narrow and that its effect on macrophages is fully reversible in 16 h in vivo. Since the immune system function exerted by Kupffer cells is restored in a relatively brief time, no immune depression is induced.

Table 1 shows details on different pretreatment time points of the experiments shown in FIG. 10.

TABLE 1

| | 2 h pretreatment | | 4 h pretreatment | | 16 h pretreatment | |
|---|---|---|---|---|---|---|
| Conditions | + | − | + | − | + | − |
| Lung/Liver | 0.394 | 1.002 | 1.03 | 2.225 | 0.360 | 0.297 |
| P Value | 0.041 | | 0.044 | | 0.514 | |

The results herein disclosed show the capability of the MPNs to transiently and safely inhibit the phagocytic activity of Kupffer cells. This activity may be exerted also on other kind of macrophages. The transient inhibition of the cell phagocytic activity upon administration of the nanoparticles allows secondary administered nanoparticles diverting from the liver to the actual biological target—the pathological tissue.

With respect to other strategies to obtain macrophage blockade, the key advantage herein shown is the use of nanoparticles comprising methyl palmitate as the active compound. In the scientific publication Sun et al., (2017) "Improved tumor uptake by optimizing liposome based RES blockade strategy" *Theranostics,* 319-328, empty liposomes are used to inhibit the phagocytic activity of the macrophages. This strategy is not immunomodulatory and inhibits phagocytosis by filling up the cells and inducing a cellular quiescent state. Also, the strategy disclosed in such document induces the depletion of opsonins from blood leading possibly to immunodepression, as declared by the authors. De facto, liposomes used for pretreatment occupy space inside macrophages reducing phagocytic capacity and this strategy does not rely on any immunomodulatory effect. Also, as proved by the scientific publication Pervin et al. (2016) "Transient effects of empty liposomes on hepatic macrophage populations in rats"; J Toxicol Pathol, 139-144, the administration of empty liposomes could even activate these cells. As such, the conditions under which liposome-induced macrophage blockade works are still not clear.

Very differently the nanoparticles herein disclosed (MPNs) exert an immunomodulatory effect and, as such, they can also be used for the treatment of diseases wherein macrophage activity may hamper tissue integrity and/or alter tissue functionality. The nanoparticles and the compositions comprising the nanoparticles herein disclosed may be used for example in the treatment of acute or chronic inflammation, wound healing, scar formation, generation of fibrotic tissue, transplant rejection, atherosclerosis, cancer.

These are diseases usually associated with macrophages activation which is sometimes related to tissue damage (Oishi et al. (2018) "Macrophages in inflammation, repair and regeneration" International Immunology, Vol. 30, No. 11, pp. 511-528; Adhyatmike et al. (2015) "The elusive Antifibrotic Macrophage" Frontiers in Medicine, Vol. 2, Article 81; Mokos et al. (2017) "Current Therapeutic Approach to Hypertrophic Scars", Frontiers in Medicine, Vol. 4, Article 83; Moore et al. (2013) "Macrophages in atherosclerosis: a dynamic balance" Nature Reviews, V13, 709-721; Ashleigh et al. (2018) "Targeting Macrophages in Cancer: From Bench to Bedside" Frontiers in Oncology, Vol. 8, Article 49). Beside their important function to defend the host from a broad spectrum of insults, macrophages play important roles in other processes: i) tissue homeostasis, ii) tissue development, iii) tissue regeneration. In the attempt to restore tissue homeostasis, these cells could contribute to the development of the pathology through the production of mediators and substances which ultimately could promote chronic inflammation, atherosclerosis, cancer; could hamper wound healing and alter the processes leading to scar formation through the generation of more fibrotic tissue; could promote transplant rejection.

As such, modulating the macrophage activity the detrimental effect resulting from their functions may be prevented. Due to the immunomodulatory activity exerted by the nanoparticles comprising methyl palmitate on macrophages, they may be used to reduce acute and chronic inflammation, favoring the outcome of the pathologic conditions in which such inflammation occurs. This effect may be particularly relevant also in the processes of wound healing, in which the modulation of macrophages activity may be used to reduce the risk of the formation of large areas of fibrotic tissue. This may apply not only to the reparation of skin tissue but also of other tissues, like for example the heart. Maintaining heart elasticity is crucial for the restoration of its functionality after an insult.

In addition, the immunomodulation is very relevant also in the prevention of transplant rejection. Macrophages are key players in the allograft response, their role is anyway divergent, some of them promote the acceptance of the graft some others promotes the rejection (Liu et al. (2016) "Macrophages as Effectors of Acute and Chronic Allograft Injury" Curr Transplant Rep, 303-312; Jiiang et al. (2014) "Macrophages in solid organ transplantation", Vascular Cell, 6:5; Salehi et al. (2015) "The Divergent Roles of Macrophages in Solid Organ Transplantation" Curr Opin Organ Transplant, 446-453). The administration of the nanoparticles herein disclosed capable of blocking macrophages activity may be used to achieve a positive impact on the graft outcome.

Naturally, while the principle of the invention remains the same, the details of construction and the embodiments may widely vary with respect to what has been described and illustrated purely by way of example, without departing from the scope of the present invention.

The invention claimed is:

1. A composition comprising nanoparticles comprising methyl palmitate and albumin, wherein the nanoparticles comprise methyl palmitate and albumin in a weight ratio (w/w) between 5:1 and 2:1.

2. The composition according to claim 1, wherein the average diameter size of the nanoparticles is comprised between 180 nm and 240 nm.

3. A method for producing the nanoparticles according to claim 1, comprising the following steps:

preparing a first solution comprising methyl palmitate, preparing a second solution comprising albumin, adding the second solution to the first solution to obtain a third solution comprising methyl palmitate and albumin in a weight ratio (w/w) comprised between 2:2.5 and 2:20, mixing the third solution thereby allowing the production of nanoparticles in the solution, and separating the nanoparticles.

4. The method according to claim 3, wherein the separating step is carried out by centrifugation of the solution containing the nanoparticles.

5. The method according to claim 3, wherein the separating step is carried out at a temperature comprised between 4° C. and 9° C.

6. A kit comprising the composition according to claim 1 and at least one active principle or at least one imaging agent, said at least one active principle or said at least one imaging agent being contained in at least one Secondary Administered Nanoparticle, for separate and sequential use in inhibiting the phagocytic activity of the macrophages and in increasing the bioavailability of said active principle and/or said imaging agent in a mammal.

* * * * *